United States Patent [19]

Frawley, III

[11] Patent Number: 4,942,175

[45] Date of Patent: Jul. 17, 1990

[54] COMPOSITION FOR THE TREATMENT OF SUBSTANCE ABUSE

[75] Inventor: Patrick J. Frawley, III, Santa Barbara, Calif.

[73] Assignee: Schick Laboratories, Inc., Los Angeles, Calif.

[21] Appl. No.: 42,263

[22] Filed: Apr. 24, 1987

[51] Int. Cl.$^5$ ............................................. A61K 31/24
[52] U.S. Cl. .................................. 514/535; 514/536; 514/537; 514/810; 514/812
[58] Field of Search ............... 514/810, 811, 812, 535, 514/536, 537

[56] References Cited

U.S. PATENT DOCUMENTS 2,818,369 12/1957 Luduena et al. ..................... 514/535

OTHER PUBLICATIONS

Clinical Toxicology 8(2), pp. 239–243 (1975), Perry.

*Primary Examiner*—Douglas W. Robinson
*Assistant Examiner*—Zohreh A. Fay
*Attorney, Agent, or Firm*—Spensley, Horn, Jubas & Lubitz

[57] ABSTRACT

A composition suitable for use in the aversion therapy treatment of cocaine abuse. The composition has the physical characteristics, taste, and anesthetic effect similar to cocaine. The composition comprises an amount of a local anesthetic sufficient to induce a degree of anesthesia similar to that induced by cocaine. The composition further comprises a carrier compound possessing the physical characteristics of cocaine. The composition may further comprise additional components which aid in imparting the physical characteristics, odor, taste, or anesthetic effect of cocaine to the composition of the present invention.

19 Claims, No Drawings

COMPOSITION FOR THE TREATMENT OF SUBSTANCE ABUSE

BACKGROUND OF THE INVENTION

The present invention concerns a composition of matter suitable for the treatment of substance abuse. More specifically, the present invention concerns a composition of matter possessing physical characteristics similar to cocaine and being suitable for use in the aversion therapy treatment of persons who abuse cocaine.

Substance abuse refers to the use of a substance, generally chemical in nature, in a manner which is generally considered improper in view of the intended use of the substance. Substance abuse is becoming extremely widespread in today's world. Indeed, many consider the problem of substance abuse to have reached epidemic proportions. As substance abuse becomes more widespread the catastrophic effects of such substance abuse become more and more apparent to members of society. As a result of an ever increasing awareness of the catastrophic effects of substance abuse, society begins to seek methods for preventing and treating such substance abuse.

Numerous methods have been advocated over the years to aid in the treatment of those involved in various forms of substance abuse. Such methods have met with varying degrees of success.

One method which has been developed to treat those involved in substance abuse is known as aversion therapy. Aversion therapy refers to a treatment intended to discourage the undesirable activities of a person by associating such activities with unpleasant feelings or consequences. Aversion therapy starts with the premise that substance abuse begins as a result of the desire to experience certain pleasurable effects achieved through the abuse of the substance. It is the attempt to continually achieve such pleasurable effects which ultimately lead to prolonged substance abuse.

Aversion therapy attempts to overcome the desire to experience such pleasurable effects by associating such abuse with negative, unpleasurable feelings Typically, a person undergoing aversion therapy for substance abuse is allowed to use or at least go through the procedure associated with using the abused substance. At the point of use or shortly thereafter, unpleasurable feelings or consequences are introduced by extraneous means. It is generally desirable that the person not experience the pleasurable effects normally associated with substance abuse. For example, in the aversion therapy treatment of people who abuse alcohol, the person is allowed to ingest alcohol Prior to ingestion, the person is given an injection which causes uncomfortable physical sensations which ultimately lead to the expulsion of the alcohol.

In the past, aversion therapy has not been available for treatment of the abuse of a wide range of substances. It is not believed that a completely satisfactory composition has been available for use in the aversion therapy treatment for cocaine abuse.

SUMMARY OF THE INVENTION

It is an object of the present invention to produce a composition suitable for use in the treatment of cocaine abuse through aversion therapy. It is preferable that such a composition be similar to cocaine in physical characteristics, anesthetic effect and the like. It is also necessary that such a composition be suitable for human use at levels dictated by the requirements of aversion therapy treatment. It is desirable that such a composition produce at least some of the physical sensations associated with cocaine abuse. However, it should not produce the pleasurable "high" typically associated with cocaine abuse. The composition desirably produces the anesthetic effect associated with the use of cocaine. By providing a composition which is similar in physical characteristics, anesthetic effect, and the like, to cocaine, it is possible to create the desired association between the use of such a composition and the use of cocaine in order to successfully treat the abuse of cocaine through aversion therapy.

These and other goals are met by providing a composition comprising a carrier compound possessing physical characteristics similar to cocaine and a local anesthetic.

DETAILED DESCRIPTION OF THE INVENTION

As used herein, the term "cocaine" refers to the powder form of an alkaloid having the formula $C_{17}H_{21}NO_4$ obtained from cocoa leaves. It is understood that the term "cocaine" is intended to encompass the powdered form of pure cocaine as well as cocaine in the form typically employed by those who abuse cocaine That is, a powdery substance comprising cocaine and one or more generally white powdery substances used to dilute or cut the concentration of the pure cocaine.

The composition of the present invention typically comprises a majority of a carrier compound. Carrier compounds suitable for use in the present invention should have generally the same appearance and tactilely perceived physical characteristics as cocaine. The carrier compound must be safe for human ingestion and/or absorption in amounts up to about 100 grams. It is also desirable that the carrier compound not interfere with the achievement of other characteristics desirably possessed by the composition of the present invention. Exemplary of suitable carrier compounds are alcohols commonly regarded as sugars such as mannitol, inositol, and the like; carbohydrates such as the saccharides, the starches and the like; celluose derivatives; and the like. It is understood that the carrier compound may be a single compound or a mixture of one or more compounds. Beneficially, the carrier compound is selected from the group consisting of mannitol, inositol and mixtures thereof. Preferably, the carrier compound is mannitol.

Cocaine is known for use as a local anesthetic. That is, cocaine is capable of producing an anesthetic effect upon topical application to human tissues. It is desirable that the composition of the present invention produce an anesthetic effect similar to that produced by cocaine. To this end, the composition of the present invention contains an amount of a local anesthetic. The amount of local anesthetic varies depending on the particular local anesthetic used but, in any event, is used in an amount sufficient to produce a numbing effect when topically applied to human tissues. Since those who abuse cocaine typically inhale or snort the cocaine, the numbing effect usually associated with the use of cocaine occurs in the nasal passages and surrounding tissues. It is therefore desirable that the numbing effect produced by the composition of the present invention be similar to the numbing effect produced on the nasal passages by cocaine upon inhalation of an amount of cocaine.

A variety of chemical compounds capable of producing a local anesthetic effect are known in the art. Such compounds are known generally as local anesthetics. Any of a number of local anesthetics or mixtures of local anesthetics capable of producing a numbing effect similar to that produced by the inhalation of cocaine is suitable for use in the present invention provided said anesthetic is safe for human use at dosage levels necessary to produce the desired anesthetic effect. Exemplary of suitable anesthetics are tetracaine, procaine, and the like. It is of course desirable that the local anesthetic have physical characteristics which do not interfere with the composition of the present invention having the physical characteristics, anesthetic effect, and the like of cocaine. Therefore, it is desired that the local anesthetic employed be colorless or white, be available in powder form and be relatively odorless. For this reason, the ease of availability, as well as the ability to achieve the desired degree of anesthesia at a relatively low dosage level, the preferred local anesthetic is tetracaine.

The compositions of the present invention suitably comprise from about 50 to about 99.5 weight percent, beneficially from about 80 to about 99 weight percent and preferably from about 90 to about 99 weight percent, based on total composition weight, of the carrier compound. The local anesthetic is suitably present in the composition of the present invention in an amount of from about 0.5 to about 10 weight percent beneficially, from about 0.5 to about 5 weight percent and preferably, from about 1 to about 3 weight percent, based on total composition weight.

It is understood that the composition of the present invention may contain such other optional ingredients as deemed desirable to produce a composition having the physical characteristics, taste, and anesthetic effect of cocaine. Such optional ingredients will generally be present in the compositions of the present invention in relatively minor quantities. That is, in amounts of from 0 to about 10 weight percent.

In one preferred embodiment of the present invention wherein the carrier compound is mannitol and the local anesthetic is tetracaine, it has been found desirable to include from about 0.5 to about 1.5 weight percent based on total composition weight, of quinine in the composition in order to impart a generally bitter taste which more closely resembles that of cocaine and to mask the relatively sweet taste associated with mannitol. In this embodiment of the present invention, quinine is used in an amount of about 1 weight percent, mannitol is present in the composition in an amount of about 97 weight percent, and tetracaine is present in the composition in an amount of about 2 weight percent, based on total weight of the composition. This embodiment has been found to be sufficiently similar to cocaine in physical characteristics, taste, and anesthetic effect to be useful in the treatment of cocaine abuse through aversion therapy.

In order to more closely imitate the odor associated with cocaine, it is often desirable to employ a scenting agent which scenting agent possesses a scent similar to the scent of cocaine. Exemplary of such a scenting agent is "Psychem" commercially available from Old Factory Incorporated. If the scenting agent employed in the compositions of the present invention is a liquid it has been found expedient to apply such a liquid scenting agent to the fingers of the person using the compositions of the present invention or to instruments employed in the inhalation of the compositions of the present invention. If the scenting agent employed in the compositions of the present invention is a powder, said powder is easily admixed directly with the other components of the composition of the present invention.

The composition of the present invention are prepared by intimately mixing the compounds which comprise the composition of the present invention. Any method suitable for mixing which method produces a generally homogeneous mixture is suitable for use in the present invention.

As is apparent from the foregoing specification, the present invention is susceptible of being embodied with various alterations and modifications which may differ particularly from those that have been described in the preceding specification. For this reason, it is to be understood that all of the foregoing is intended to be merely illustrative and is not to be construed or interpreted as being restrictive or otherwise limiting of the present invention, excepting as it is set forth and defined in the following claims.

What is claimed is:

1. A powdered composition suitable for use in the aversion therapy treatment of cocaine abuse, the composition consisting essentially of:
   (A) from about 1.0 to about 3.0 weight percent, based on total composition weight, of a local anesthetic selected from the group consisting of tetracaine, procaine and mixtures thereof; and
   (B) from about 95 to about 99 weight percent, based on total composition weight, of a carrier compound selected from the group consisting of mannitol, inositol and mixtures thereof.

2. The composition of claim 1 wherein the local anesthetic is tetracaine.

3. The composition of claim 1 wherein the carrier compound is mannitol.

4. The composition of claim 3 wherein the local anesthetic is tetracaine.

5. The composition of claim 4 wherein the composition further comprises an amount of quinine.

6. The composition of claim 5 wherein the quinine is present in an amount of from about 0.5 to about 1.5 weight percent based on total composition weight.

7. A powdered composition suitable for use in the aversion therapy treatment of cocaine abuse, the composition consisting essentially of:
   (A) from about 1.0 to about 3.0 weight percent, based on total composition weight, of tetracaine;
   (B) from about 97 to about 99 weight percent, based on total composition weight, of mannitol; and
   (C) about 1.0 weight percent, based on total composition weight, of quinine.

8. A method of treating cocaine abuse which comprises administering a powdered composition suitable for use in the aversion therapy treatment of cocaine abuse, the composition consisting essentially of:
   (A) an amount of local anesthetic sufficient to induce a desirable degree of anesthesia, wherein the amount of local anesthetic is from about 0.5 to about 5.0 weight percent based on total composition weight; and
   (B) a majority of a carrier compound possessing physical characteristics similar to cocaine, wherein the amount of carrier compound is from about 80 to about 99 weight percent based on total composition weight.

9. The method of claim 8 wherein the composition is similar in physical characteristics, taste, and anesthetic effect to cocaine.

10. The method of claim 8 wherein the desirable degree of anesthesia is that degree of anesthesia which is similar to the degree of anesthesia induced by cocaine.

11. The method of claim 8 wherein the local anesthetic is selected from the group consisting of tetracaine, procaine and mixtures thereof.

12. The method of claim 8 wherein the carrier compound is selected from the group consisting of mannitol, inositol and mixtures thereof.

13. A method of treating cocaine abuse which comprises administering a powdered composition suitable for use in the aversion therapy treatment of cocaine abuse, the composition consisting essentially of:
   (A) from about 1.0 to about 3.0 weight percent, based on total composition weight, of a local anesthetic selected from the group consisting of tetracaine, procaine and mixtures thereof; and
   (B) from about 95 to about 99 weight percent, based on total composition weight, of a carrier compound selected from the group consisting of mannitol, inositol and mixtures thereof.

14. The method of claim 13 wherein the local anesthetic is tetracaine.

15. The method of claim 13 wherein the carrier compound is mannitol.

16. The method of claim 15 wherein the local anesthetic is tetracaine.

17. The method of claim 16 wherein the composition further comprises an amount of quinine.

18. The method of claim 17 wherein the quinine is present in an amount of from about 0.5 to about 1.5 weight percent based on total composition weight.

19. A method of treating cocaine abuse which comprises administering a powdered composition suitable for use in the aversion therapy treatment of cocaine abuse, the composition consisting essentially of:
   (A) from about 1.0 to about 3.0 weight percent, based on total composition weight, of tetracaine;
   (B) from about 97 to about 99 weight percent, based on total composition weight, of mannitol; and
   (C) about 1.0 weight percent, based on total composition weight, of quinine.

* * * * *